United States Patent [19]
d'Agraives et al.

[11] Patent Number: 5,807,048
[45] Date of Patent: Sep. 15, 1998

[54] SEALING FASTENER WITH ULTRASONIC IDENTIFIER AND REMOVAL ATTEMPT INDICATOR, AND ULTRASONIC READING DEVICE FOR SAME

[75] Inventors: Bertrand Causse d'Agraives, Laveno; Jan Toornvliet, Orino; Ermanno Mascetti, Germignaga, all of Italy

[73] Assignee: European Atomic Energy Community (EURATOM), Luxembourg, Luxembourg

[21] Appl. No.: 914,242

[22] Filed: Aug. 19, 1997

Related U.S. Application Data

[63] Continuation of Ser. No. 392,915, Apr. 24, 1995.

[30] Foreign Application Priority Data

Sep. 3, 1992 [GB] United Kingdom ............... 921866

[51] Int. Cl.$^6$ .................................... F16B 31/00
[52] U.S. Cl. .................... 411/2; 411/4; 411/14; 73/761
[58] Field of Search ............... 411/2–5, 14, 910; 73/760, 761, 763, 627

[56] References Cited

U.S. PATENT DOCUMENTS

| | | | |
|---|---|---|---|
| 3,977,236 | 8/1976 | Raatz, Jr. et al. | 73/761 |
| 3,987,668 | 10/1976 | Popenoe | 411/14 X |
| 4,014,208 | 3/1977 | Moore et al. | 73/761 |
| 4,294,122 | 10/1981 | Couchman | 73/761 |
| 4,569,229 | 2/1986 | de Halleux | 73/761 X |
| 4,649,753 | 3/1987 | Goodsmith | 73/761 X |
| 5,018,988 | 5/1991 | Kibblewhite et al. | 73/761 X |
| 5,131,276 | 7/1992 | Kibblewhite | 73/761 |
| 5,220,839 | 6/1993 | Kibblewhite | 73/761 |
| 5,228,250 | 7/1993 | Kibblewhite | 411/5 X |
| 5,256,015 | 10/1993 | St. Clair | 411/4 |
| 5,343,785 | 9/1994 | Holt et al. | 73/761 X |

FOREIGN PATENT DOCUMENTS

| | | |
|---|---|---|
| 035323 | 9/1981 | European Pat. Off. . |
| 445506 | 9/1991 | European Pat. Off. . |
| 2403635 | 8/1975 | Germany . |
| 2067699 | 7/1981 | United Kingdom . |

*Primary Examiner*—Suzanne Dino
*Attorney, Agent, or Firm*—Bacon & Thomas

[57] ABSTRACT

A sealing fastener includes a unique identifier device for the individual fastener that enables ultrasonic identification of the device using an ultrasonic fault measuring system, and a frangible element within the fastener integrated with the identifier device that provides an ultrasonic signature indicating an attempt to loosen or remove the fastener when subjected to an ultrasonic signal generated by an ultrasonic fault measuring system. The unique identifier device includes a stack of individual metallic washer elements brazed together, with each washer element including discontinuities or cavities that are randomly arranged with respect to the cavities of the other washers in the stack. The fastener includes relatively movable portions that cause fracture of the frangible element upon any attempt to loosen or remove a fastener after it has been tightened or secured at its sealing location. An ultrasonic reading device includes an adapter that cooperates with the fastener to precisely locate an ultrasonic transducer with respect to the identifier and indicator so that a signature of the identifier and the indicator can be obtained in a single step using a single ultrasonic reading head associated with an ultrasonic fault detector system.

17 Claims, 12 Drawing Sheets

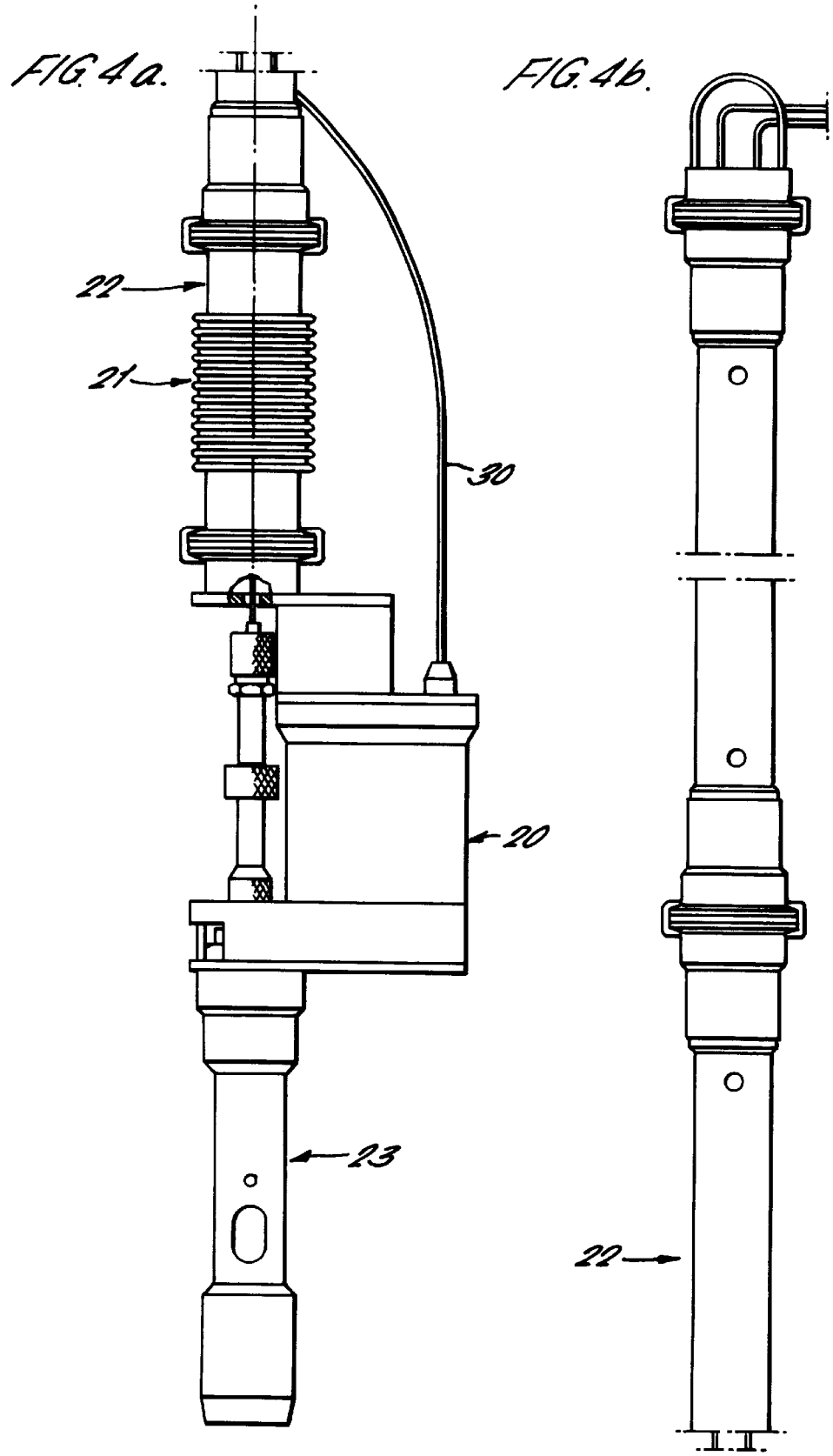

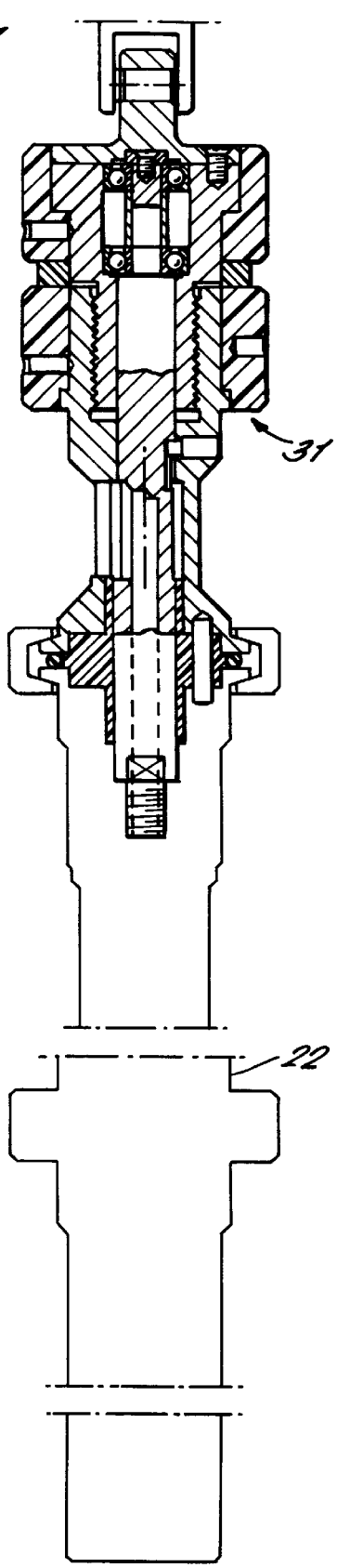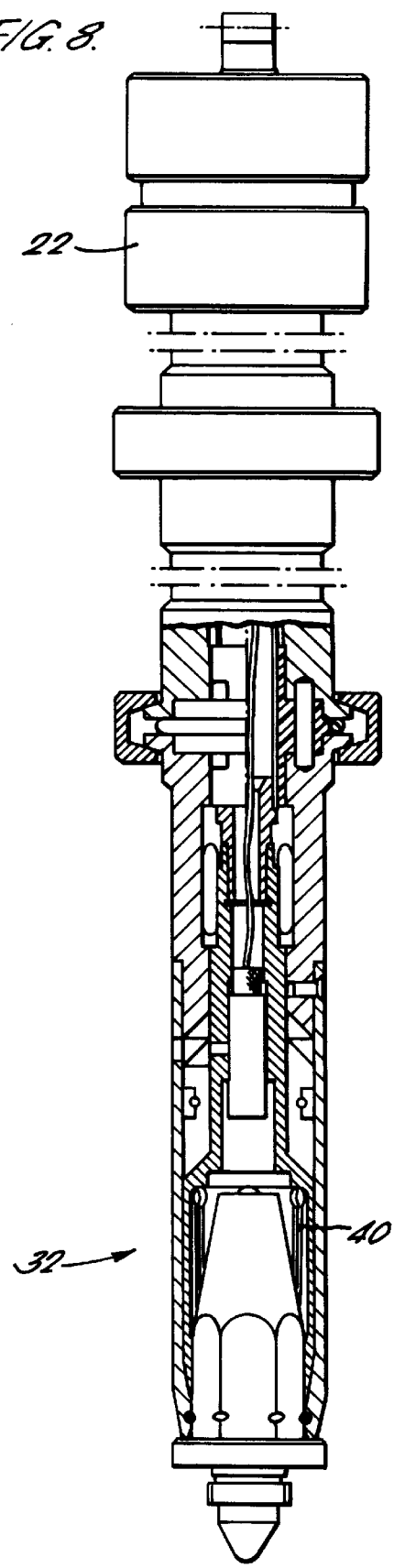

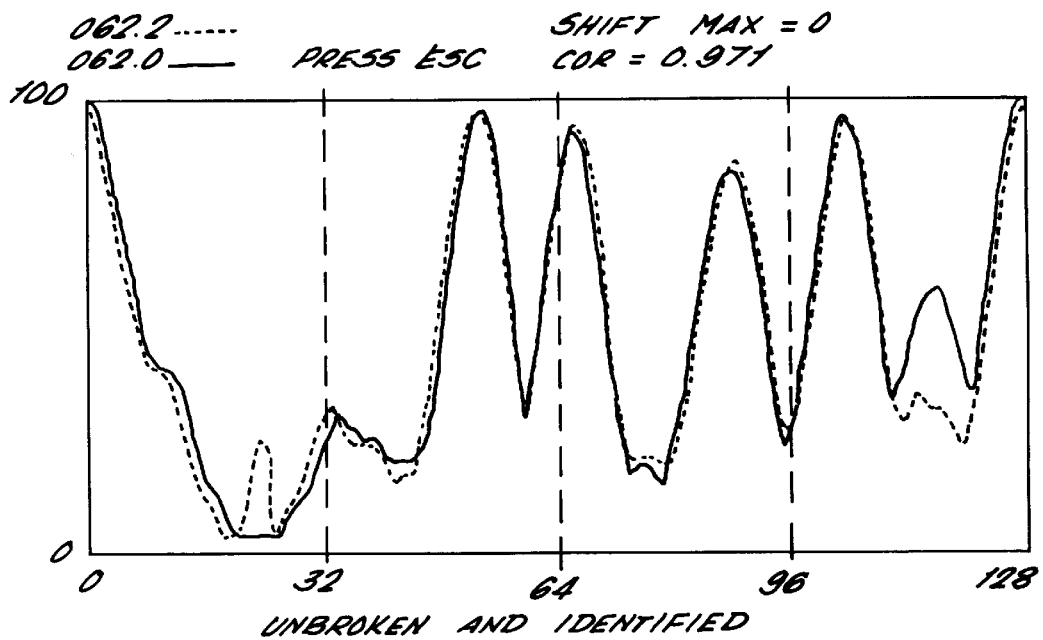

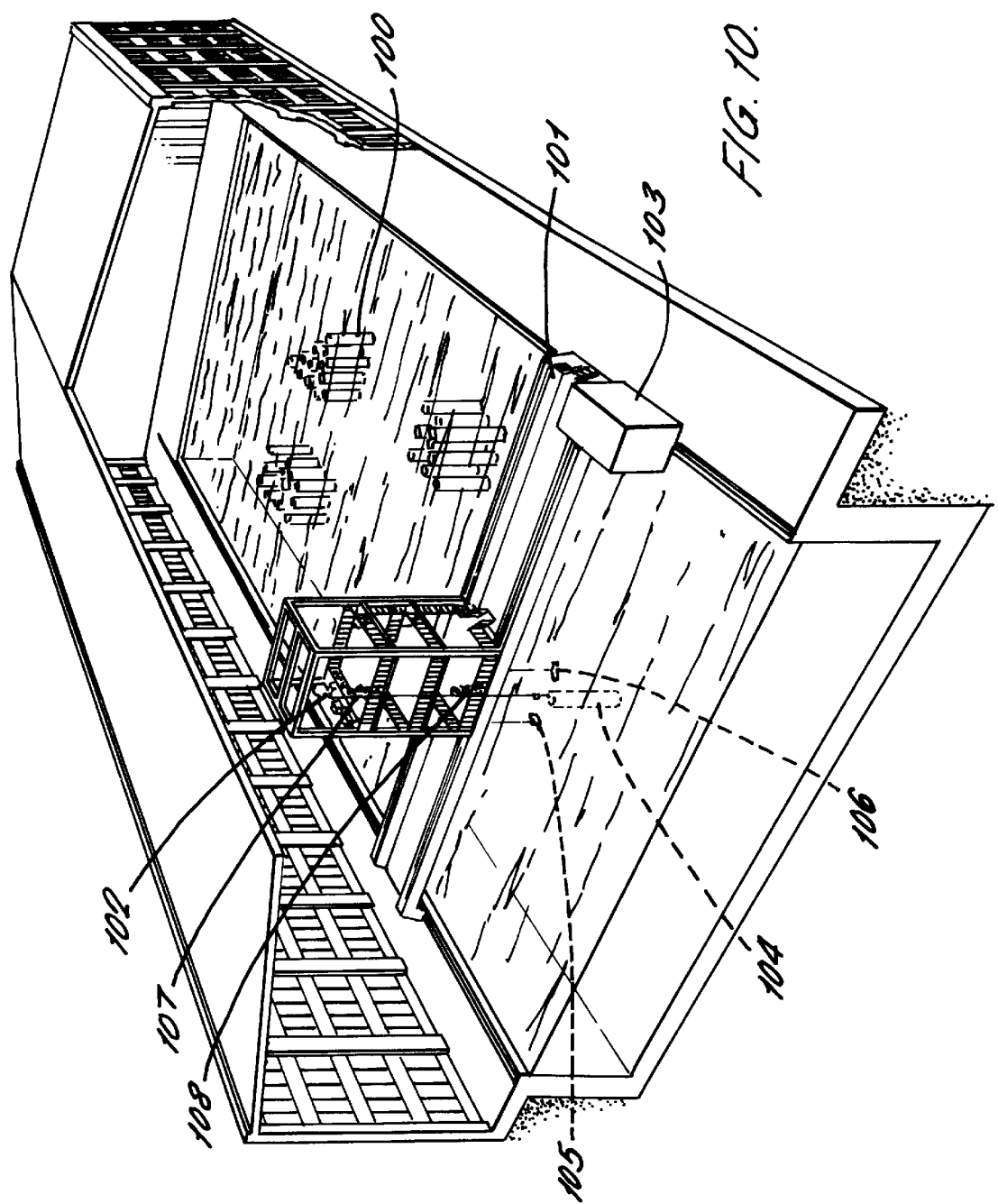

SEALING FASTENER WITH ULTRASONIC IDENTIFIER AND REMOVAL ATTEMPT INDICATOR, AND ULTRASONIC READING DEVICE FOR SAME

This application is a continuation application Ser. No. 08/392,915, filed Apr. 24, 1995.

BACKGROUND OF THE INVENTION

1. Field of the Invention

The present invention relates to ultrasonic sealing bolts and identification bolts for use in sealing containers holding dangerous substances or sensitive or valuable materials, for example, fissile materials.

Within the framework of Nuclear Safeguards, there is a demand for a robust and durable system of seals making possible the monitoring, identification and verification, over a period of several years, of containers used for the conveyance and then storage under water of fissile materials to be reprocessed.

There is also a demand for an identification system, for example, for nuclear transportation casks, or for other movable structures of strategic value (containers, underframes, guns, etc.) which have to be supervised or indexed. This system will have to use, as "markers", elements which can withstand the severe operating conditions of the structure on which they are mounted.

2. Discussion of the Prior Art

The idea of using a random distribution of defects in a stable structure for recognition by ultrasonic means is already known and is derived directly from non-destructive testing techniques. At the beginning of the 1980s, the applicants studied various solutions and, in particular, prototype seals for fuel elements. The initial solutions encountered problems in respect of the reproducibility of the identity reading and were not provided with integrity control. These systems are such that it is not possible to identify a "broken" seal. A solution is used in Canada for steady stacks of irradiated fuel elements, based on another method of generating an ultrasonically measurable random signature. However, this kind of seal cannot be identified once it has been broken.

Further prior art is described in GB-A-2,067,699 which discloses a tamper-proof system primarily intended to seal commodity meters. A bolt has a two part head held together by a breakzone such that when the bolt is fastened to a given torque, the breakzone fractures and the head is free to move in a plastic cup. If the bolt is to be unfastened, the head must be disengaged from the cup and this can only be achieved by damaging the cup visibly, thus indicating tampering.

U.S. Pat. No. 4,294,122 describes a bolt and an apparatus for mounting the bolt. The purpose of the combination of bolt and mounting apparatus is to fasten the bolt precisely at a predetermined load. A transducer is mounted in the bolt for obtaining preload measurements.

EP-A-4,455,506 discloses a system similar to that described in U.S. Pat. No. 4,294,122. The purpose of the apparatus is to mount a bolt and test its preload. There is no provision for determining the specific identity of the bolt.

The latest solutions proposed by the applicants for fuel elements resolved the two problems of reproducibility of the identity reading and introduced a device enabling integrity control to be effected. Although they are well suited to application to a boiling water fuel element (modified in the factory as required), they are not suitable for direct mounting on containers with bolted-on covers.

SUMMARY OF THE INVENTION

According to the present invention there is provided a sealing bolt or fastener means for sealing the lid of a container to the body of a container, the sealing bolt or fastener means comprising a head and a body which interlocks the lid and body of the container, the internal structure of the head being constructed such that it is at least partially deformed when an attempt is made to remove the sealing bolt means from the container onto which the bolt has been secured and tightened, and wherein the internal structure of the head comprises a plurality of randomly arranged stacked discs, each disc having one or more voids therein for providing a specific identity for each sealing bolt means.

Preferably, the body of the sealing bolt has a threaded shank which can be threaded into the container.

Preferably, the body of the sealing bolt is hollow and comprises clamping elements to secure the sealing bolt means to a container having a pre-installed dowel or pin interlocking the lid and body of the container.

Preferably, the internal structure of the head comprises a pattern of cavities which can be sensed ultrasonically to identify the bolt or fastener.

Preferably, the sealing bolt means further comprises a frangible element within the internal structure of the head which breaks at a predetermined location when an attempt is made to remove the sealing bolt means from the container.

Preferably, the frangible element has a region of reduced thickness thereby providing a weak point in the element.

Preferably, the head is adapted to co-operate with a reading device which can not only identify the bolt means but which can also generate an ultrasonic signal and compare the ultrasonic signal reflected by the internal structure of an untampered sealing bolt means with that reflected by a tampered sealing bolt means or a sealing bolt means which has become loosened after having been tightened adequately.

The present invention also provides a reading device for use with a sealing bolt means as described herein comprising a transducer which can generate an ultrasonic signal and sense the signal reflected by the internal structure of the sealing bolt means.

In a further aspect, the present invention provides a method of testing for tampering of a sealing bolt means for a container comprising the steps of applying a reading means to the head of a sealing bolt means, generating an ultrasonic signal and sensing the signal reflected from the internal structure of the sealing bolt means, and comparing the reflected signal with the signal reflected from an untampered sealing bolt means to determine whether tampering has occurred or whether the sealing bolt means has been untightened.

Preferably, both the specific identity and the integrity of the internal structure of the bolt means can be read simultaneously.

The present invention also provides a reading device for determining the identity and/or integrity of the internal structure of a sealing bolt means, the device comprising a reading head, means for fitting the reading device to a sealing bolt means, a transducer and an ultrasonic signal generating means, wherein the transducer rotates in close vicinity to the sealing bolt means thereby recording the ultrasonic signal reflected from the internal structure of the sealing bolt means.

The present invention is based on the substitution of one (or more) of the standard bolts for container covers with one (or more) individually identifiable "special" bolts, which make it possible to verify, when inspected, whether or not they have been unscrewed or removed for fraudulent or unauthorized opening. The basic idea was to attempt to incorporate the essential elements of a fuel element seal, namely the identity marking and the integrity control device, within an assembly which still retains the mechanical function of an ordinary bolt.

BRIEF DESCRIPTION OF THE DRAWINGS

A preferred embodiment of the present invention will now be described in detail, by way of example only, with reference to the accompanying drawings, of which:

FIG. 2b is a cross sectional view and FIG. 2c is a view from below;

FIG. 4a and 4b depict the bottom and top respectively of a reading device;

FIG. 7 depicts the handle of a fitting implement;

FIG. 8 depicts the clamp of a fitting implement used for both loosening and removing standard and "special" sealing bolts and installing and tightening such bolts;

FIG. 9a depicts graphically a typical signal recorded by the measuring station connected to the transducer;

FIG. 9b shows a series of operating parameters of the kind issued when using the system in a laboratory; and FIG. 10 depicts a storage pond holding a number of containers sealed by sealing bolts in accordance with the present invention;

DETAILED DESCRIPTION OF THE PREFERRED EMBODIMENTS

Figure 1:
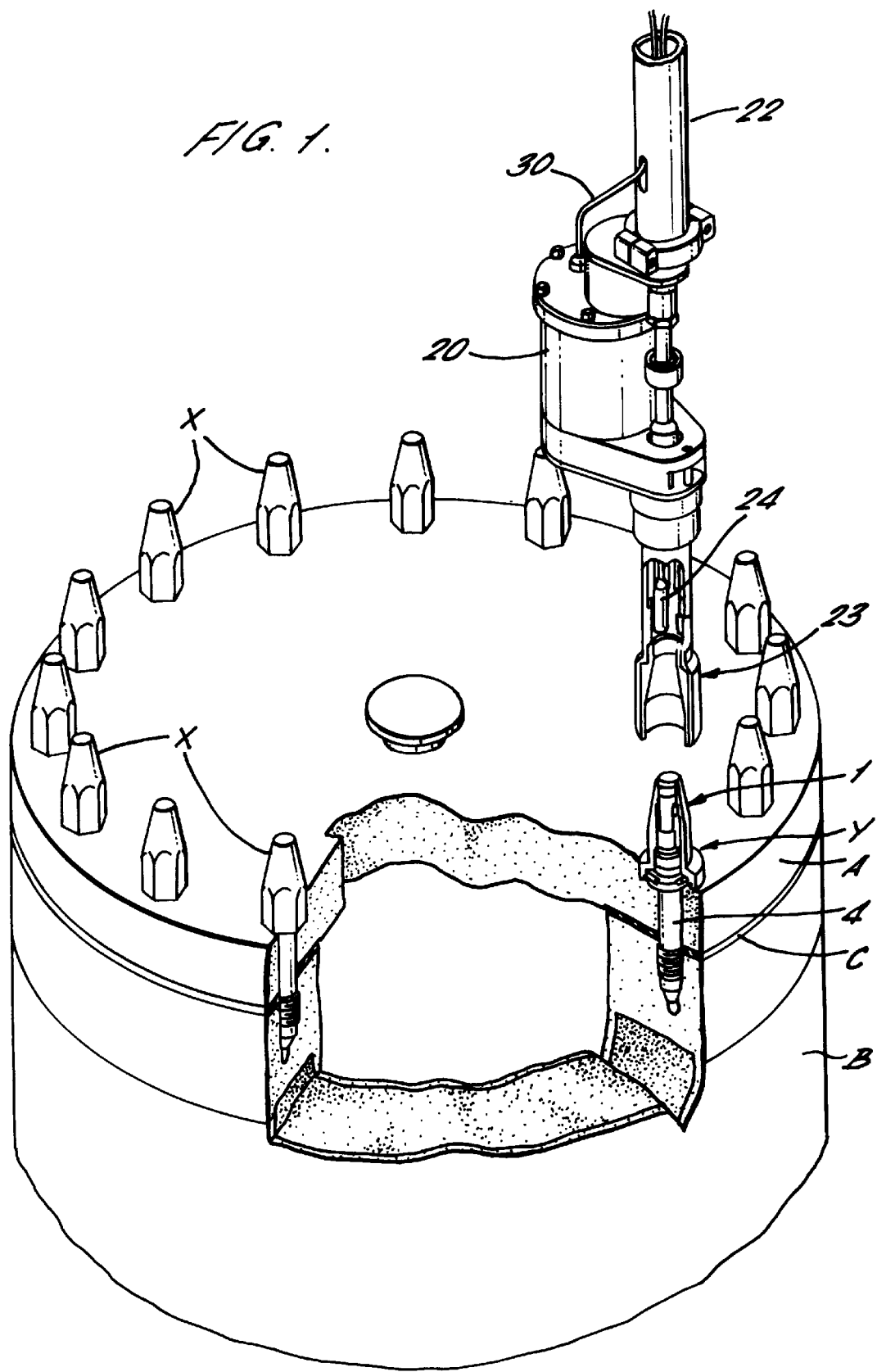
FIG. 1 depicts a container sealed by a number of standard sealing bolts and a reading device, one of the sealing bolts being constructed in accordance with the present invention.

A sealing-bolt Y in accordance with the present invention, is shown in FIG. 1, in which the hexagonal head or driving connection 1 of the bolt ends in a cone (similar to the cone of a standard bolt "X") to enable the precise fitting of the reading device on the bolt. The "special" bolts "Y" have the same appearance and can be installed and tightened by the operator in the same manner and with the same torque as the standard bolts "X" which they replace.

The standard bolts X are shown in FIG. 1 as well as a "special" bolt Y. The standard bolts X and "special" bolt Y seal the lid A to the body B of a container—a gasket C being located between the lid A and body B.

Figure 12A:
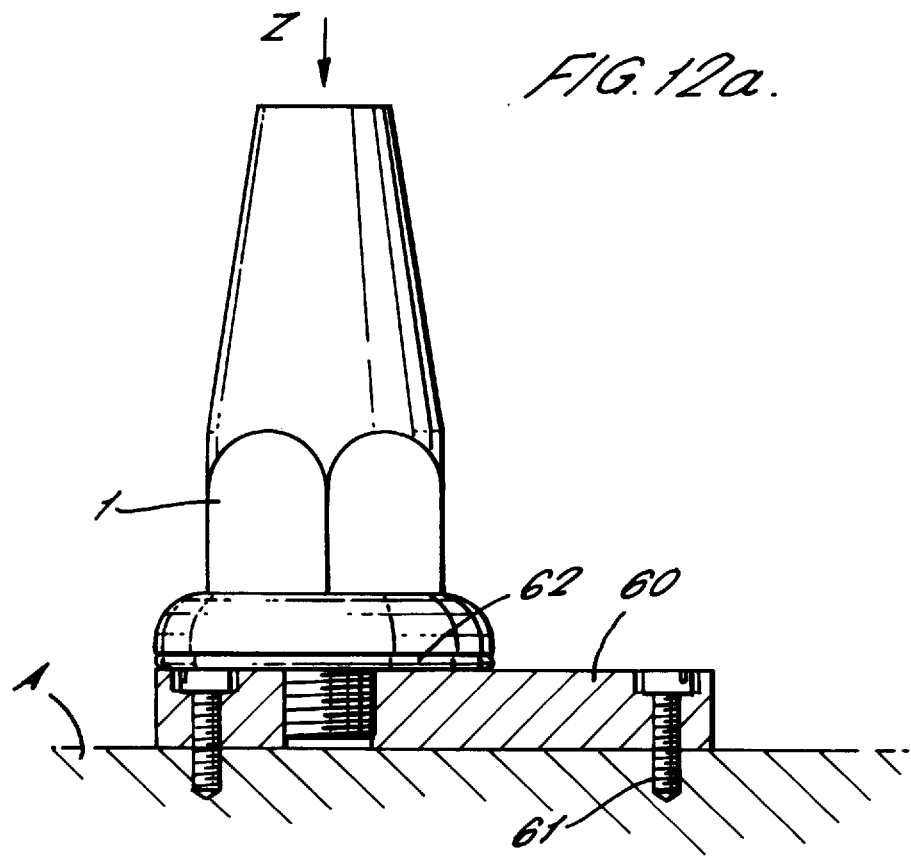
FIG. 12a and FIG. 12b show respectively in perspective view and in a view downwardly in a direction Z; a sealing bolt in accordance with the present invention secured to a container by an intermediate element.

For the bolt or seal identification system, the proposed solution is based on screwing a sealing bolt directly on to the structure to be "marked" (identified) or by means of a non-detachable intermediate member (see FIG. 12a).

Figure 3:
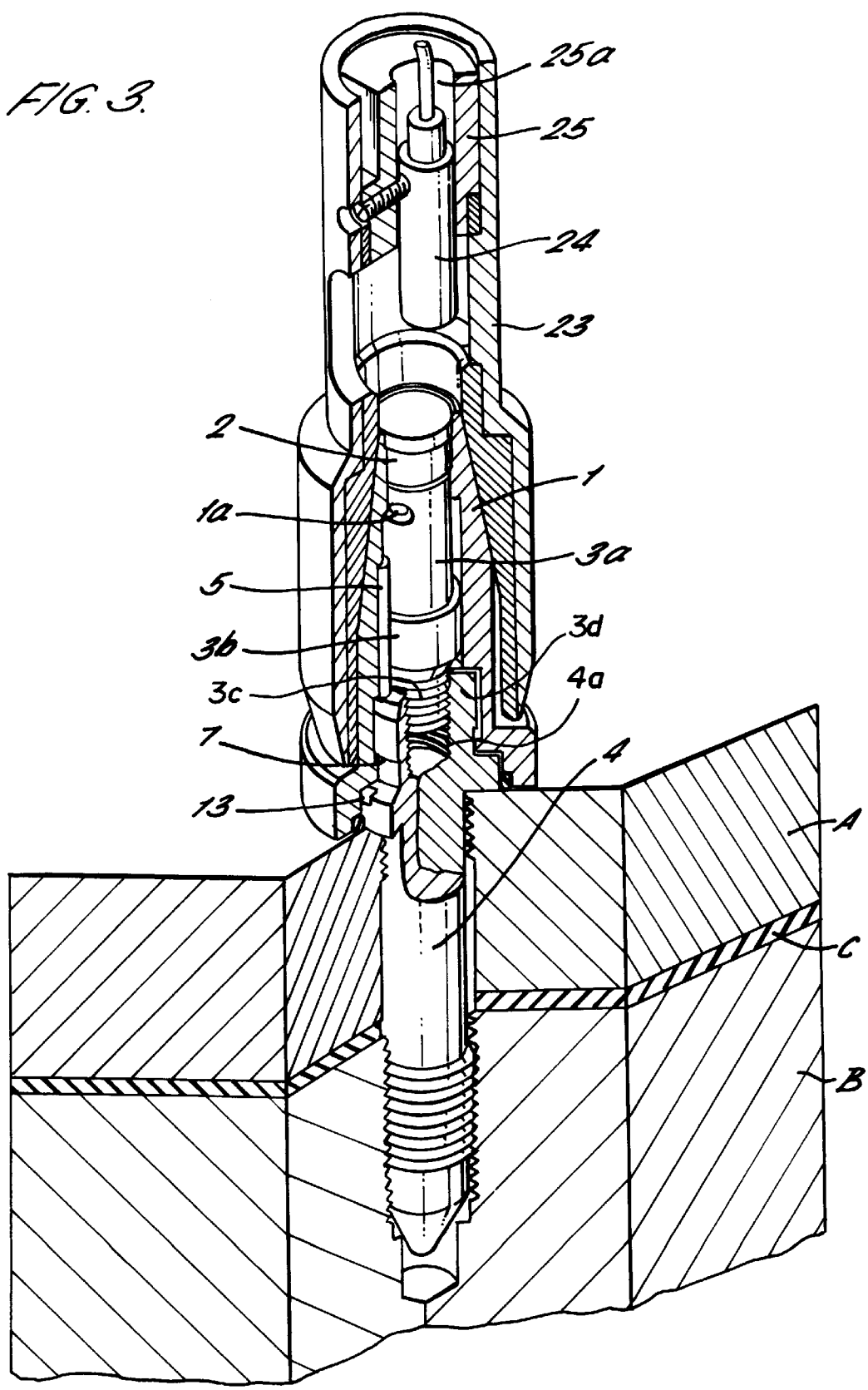
FIG. 3 shows details of the sealing-bolt of the present invention fitted to the adapter of a reading head as during verification.

In addition to the sealing bolt Y itself, the solution comprises developing a complete system for its installation, identification and integrity verification and removal, these operations having to be able to be carried out under water or in the open air. In fact, the reading head of the reading device is the essential implement enabling verification of identity and integrity of the sealing bolt to be effected. It was designed specifically to allow the examination of this type of seal bolt and the scanning of its identity by a transducer rotating under accurate relative positioning conditions. As is evident from FIGS. 1 and 3, repositioning accuracy of the ultrasonic reader is achieved by means of an adapter 23 which ensures perfect cone-to-cone fitting between reader and bolt "Y", whatever the length of the ultrasonic implement, as well as by means of accurate guidance of the transducer-holder barrel 25 (FIG. 3).

Figure 2A:
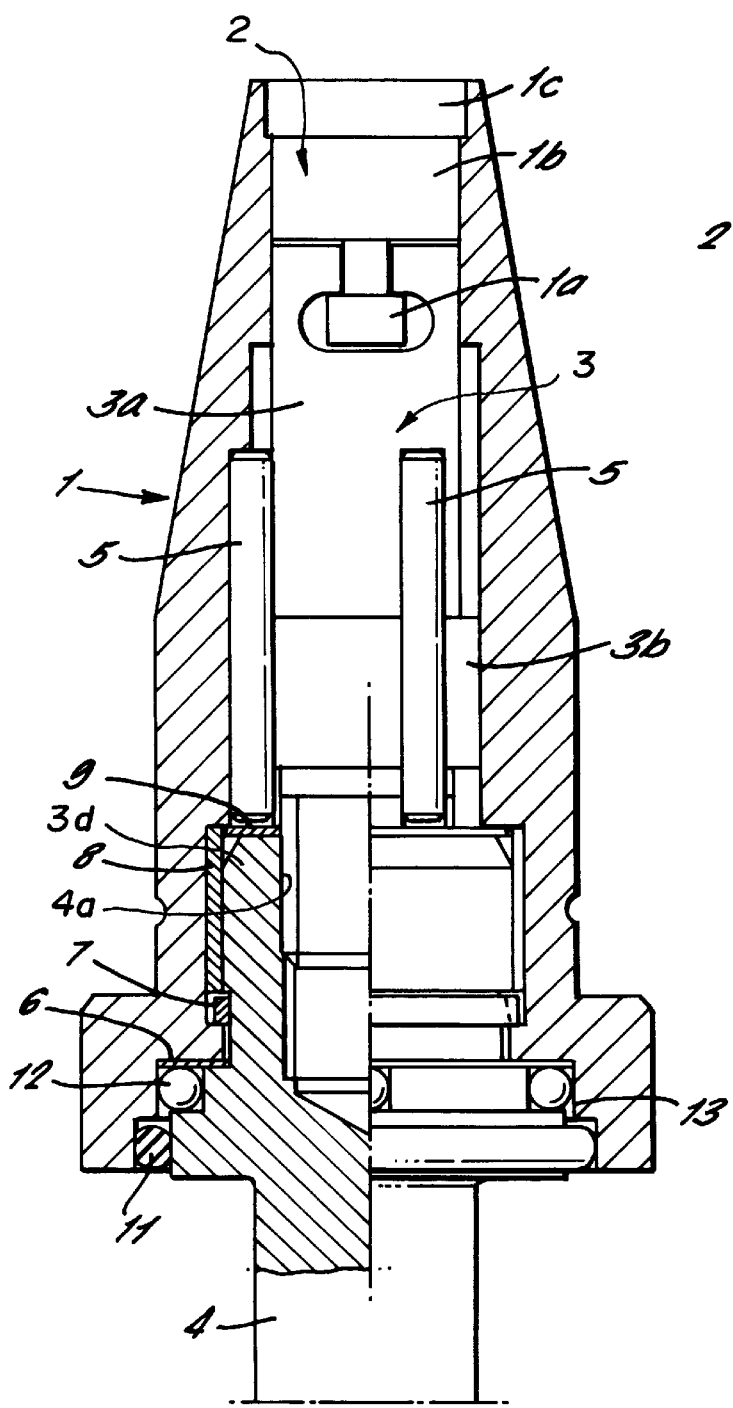
FIG. 2a is a cross sectional view of a preferred embodiment of a sealing bolt in accordance with the present invention.

FIG. 2a is a preferred embodiment of a sealing-bolt Y having a driving connection or for enabling driving of the bolt by a suitable driver device and a long shank or a short shank 4.

Figure 2B:
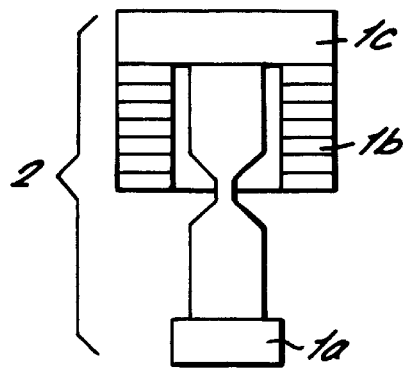
FIG. 2b and FIG. 2c show details of the component (2) in FIG. 2a where
Figure 2C:
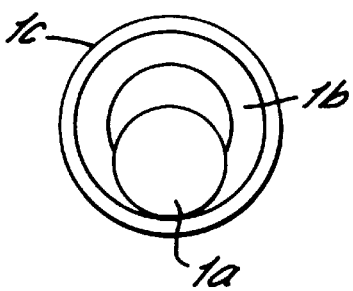

The sealing-bolt comprises a seal "core" which is component 2, the core incorporating in a limited volume, a delay line block 1c, a stack of disks 1b providing a scattering of cavities that uniquely cause ultrasonic echoes generating a unique signature for the bolt, as well as a frangible bar 1a, rupture of which can be detected ultrasonically. The core is produced in accordance with a production process involving, inter alia, brazing an assembly of small steel washers 1b that are randomly notched and stacked in random manner to provide a unique ultrasonic signature for the bolt or fastener in which the core is assembled, and a delay line block 1c provided with a frangible bar 1a integrally incorporated in the component. Details of the component 2 can be seen in FIGS. 2b and 2c. It will be noted that the frangible breaking bar 1a is eccentric of the centerline of the disks for enabling ultrasonic reading by an eccentrically mounted transducer as described below. The cylindrical "core" 2 with a volume of approximately 1 cm$^3$ represents and is located along the "centre" of the sealing bolt Y. It is coaxially mounted with and is welded to the top of the bolt head 1 which is the upper portion of the bolt. The reading head adapter (sometimes referred to herein as a coupling element) of the reading device (FIG. 3), which is fitted on to the conical part of the head 1 at the moment of ultrasonic verification, enables a transducer 23 incorporated therein to rotate (actually orbit) eccentrically of the centerline of the bolt at a given distance (approximately 2.5 cm) from the core 2, over a small orbit circle (with a radius of approximately 3.5 mm) to thereby enable it to examine, during a single revolution, both the cavities defining the unique identity signature of the bolt and the integrity of the reduced section of the breaking bar 1a.

A one-way rotating mechanism 13 connects the head 1 and the shank 2 and makes it possible to transmit, by means of jamming balls 12, to the shank 4 and in one direction the tightening torque applied to the head 1.

A tension member 3 forming a second section of head 1 includes portions 3a, 3b that connect the core 2 to the internally reversely threaded head 3d of the shank 2 as shown at 4a and makes it possible by the tension member 3 to break by tension the breaking bar 1a of the core 2 upon starting to "unscrew" the sealing-bolt with a reverse weak torque, i.e., causing it to rotate in the direction permitted by the one-way rotating mechanism 13. At the end of travel, after the bar 1a has been broken with a torque of about 20 Nm, the tension member 3b, which slides axially without relative rotation between it and the component 1 due to axial guiding rollers or key elements 5, abuts against the end of the reverse thread 4a of the shank 4 and a high unscrewing torque (about 70 Nm) can then be applied thereto through the rollers 5, which causes the sealing bolt to be unscrewed from the body of the container into which it has been screwed.

More specifically, as shown in FIGS. 2a and 3, the shank 4 of the fastener is secured to a device B to be sealed by rotating the shank in a first or "clockwise" direction in a normal sense by torquing the hexagonal driving connection at head 1 in a "clockwise" sense through the action of the one-way clutch or coupling elements 12, 13 which transfers torque from the hexagonal head 1 to the shank 4. The shank is torqued at a high setting which inhibits ready reverse or second direction rotation of the shank and remains in this position much in the same manner as a normal fastener bolt. However, initial reverse rotation of the hexagonal head 1 is not transmitted immediately to the shank 4, but rather is transmitted to the tension member 3a which has an enlarged head 3b and a reversely threaded end portion 3c that engages reverse threads 4a in the head 3d of the shank 4. Initial reverse rotation of the hexagonal head 1 thus drives the tension member 3a axially inwardly towards the shank 4 through the action of the reversely threaded end portion 3c and the reverse threads 4a in the head of the shank 4, which remains in position in device B due to the high torque setting that was previously applied to the bolt. In effect, the tension member 3a is driven downwardly into the head of the shank 4 until the enlarged head 3b of the tension member 3a engages the shoulder established by a washer 9 located at the proximal end of the head of shank 4, at which point the tension member 3a can no longer move axially. In the meantime, the axial movement of the tension member 3a has already fractured the frangible element 1a due to its axial movement, creating a situation that can be identified by an ultrasonic fault measuring system due to the dislocation of the fractured portion 1a from the remainder of the core 2. Once the enlarged head 3b is grounded against the shoulder established by the washer 9, continued reverse rotation of the hexagonal head 1 is transmitted to the tension member 3 through the anti-rotation rollers 5, which function as keys between the hexagonal head 1 and the tension member 3. Reverse torque is then transmitted directly into the head of the shank 4 such that continued reverse rotation of the hexagonal head 1 unscrews the shank 4 from the container in the normal manner. Obviously, if the hexagonal head 1 is slightly rotated to an extent sufficient to fracture the frangible bar 1a but not to an extent sufficient to remove or loosen the shank 4, an indication of tampering with or attempted loosening or removal of the sealing bolt will be evident by ultrasonically reading the ultrasonic signature of the fractured bar 1a.

Connection or intermediate components, such as jamming balls 12, clip 7, sliding rings or washers 6, 9 and bushings 8, rollers 5, O-rings 11, take care of the clamping, locking, sliding, guiding and sealing operations which are necessary for the correct operation of the assembly.

In addition to the sealing bolt, the rest of the system will also be described. FIG. 3 shows an isometric partial sectional view of the sealing bolt and also the reading head adapter or coupling element 23 in its position "fitted" on to the top of the sealing bolt at the instant of an ultrasonic reading. The adapter or coupling element 23 is essential to the accurate positioning of the transducer 24 with respect to the sealing bolt Y.

Figure 5A:
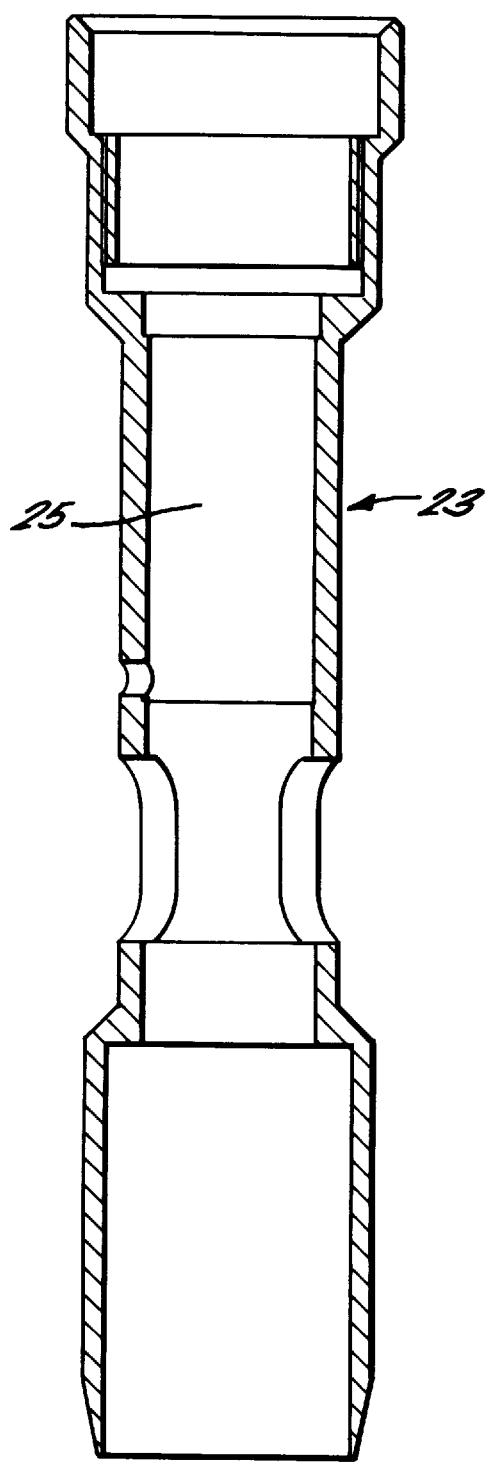
FIG. 5a shows detail of the adapter in FIG. 3
Figure 5B:
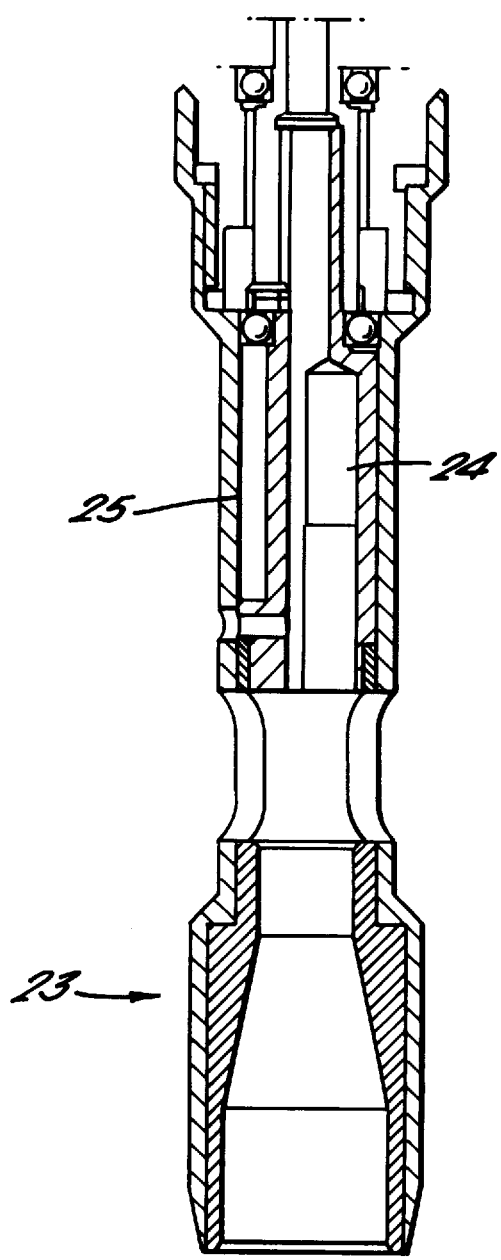
FIG. 5b shows the relative location of the transducer located therein.
Figure 6:
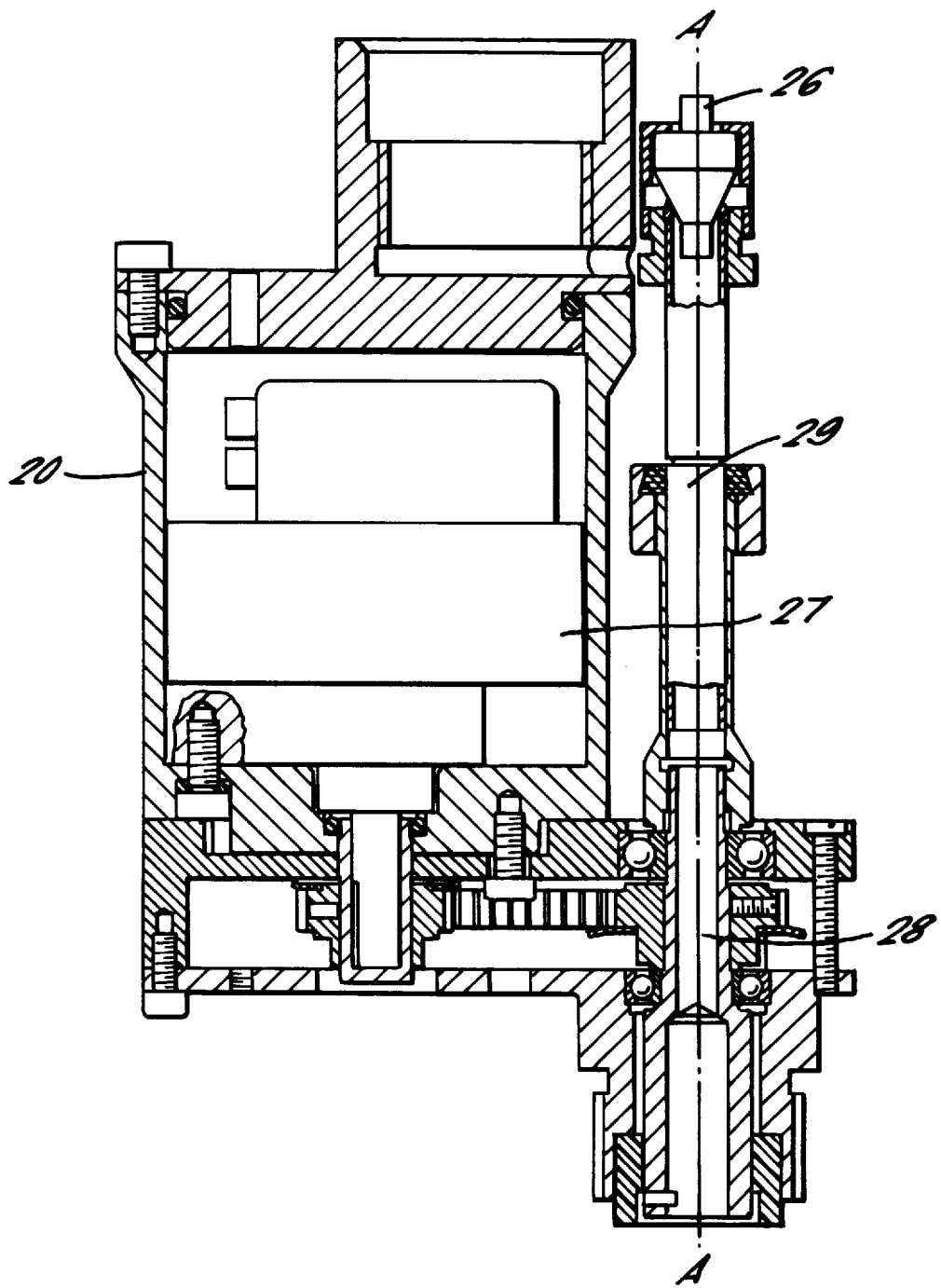
FIG. 6 is a cross sectional view of the reading device without the adapter as shown in FIG. 1.

FIGS. 4a and 4b show the external configuration of the bottom and top of a reading device. The reading head 20 is connected by bellows 21 (which is optional) to the extension tube 22 (a series of 1 to 1.5 m) for operation by the flexible bellows 21. FIGS. 5a, 5b and 6 show respectively the adapter 23 containing the transducer 24 and the reading device. The eccentric position of the reading head 20 relative to the general axis A of the reading device is to be noted, which allows a cable 30 to emerge coaxially to the transducer barrel 25 in which the transducer 24 (i.e., an ultrasonic energy transmitter and receiver) is disposed in an eccentric hole 25a (see FIG. 1). The use of a rotary electric coupling 26 in FIG. 6 ensures the electrical connection of the transducer 24 with the remote surface equipment (see FIGS. 1 and 3). FIG. 6 depicts the rotary transmission 26, a motor/reducer 27 and component 28 comprises a set of gears and belt for transmitting rotation of the motor to the shaft connected to the transducer barrel 25. A protective tubing 29 is also provided which can rotate and which allows mounting/dismounting of the transducer 24 and of the rotary transmission 26 with related connecting cable 30. The motor/reducer 27 is water-tight and component 28 can operate in water.

The reading device can be used either under water or on site, or in air conditionings such as in an office or laboratory.

FIGS. 7 and 8 show the fitting implement, having an upper part 31 (handle) and a lower part 32 (clamp), with the implement of original design making it possible to unscrew and grip a normal bolt, to fit and tighten to the correct torque a normal bolt or sealing bolt, to break and remove (or leave) a sealing bolt, where all these operations are carried out remotely at a distance of several meters, under water and, if a torque has to be controlled, by means of a torque wrench. The handle 31 and clamp 32 are separated by extension tube 22 having sections 1 to 1.5 m long which can be added according to end requirements. Inside the extension tube (22), a sliding rod is guided and can be assembled with as many extension sections as the tube (22). The sliding rod allows thrust to be transmitted to the clamp from the rotating ring of the handle by means of a threaded element. The clamp 32 is provided with six blades 40 which radially grip the hexagonal portion of the head 1 of a sealing bolt. In the embodiment depicted in FIG. 8, an optional transducer was inserted for use in cloudy waters in order to trigger a signal when the reading device is actually fitted on a sealing bolt.

To enable ultrasonic reading to take place, a measuring station uses a flaw detector of a commercial type, and to which the reading head transducer is connected. In turn, the flaw detector is connected to a computer which can control it and which is programmed with operating software which was developed by the applicants. When the transducer is caused to emit ultrasonic energy in the axial direction and to rotate above the seal bolt head, it "sees" by reflection of ultrasonic energy the random cavities previously mentioned in core 2 and the echo signal is recorded. The fault reader enters in the memory at each instant the highest peak observed in a precalibrated window. During one revolution, a signal of the type shown in FIG. 9a is thus obtained. This signal is digitized and entered in the memory. It is retrieved when effecting a signature verification and it is compared by correlation with the new quantity. If the coefficient of correlation is above a given threshold (for example 0.9), the sealing bolt is uniquely identified. Moreover, if the characteristic trough (small zone without a signal) normally indicating an intact breaking bar 1a is replaced by a hump, this is proof that the seal has been unscrewed and that its breaking bar 1a or frangible element has been broken which means that its integrity has been violated. This point is very important in this technique, since with a single reading it is possible to verify both the unique individual identity of the bolt and the integrity of the seal. FIG. 9b shows a series of 9 operating parameters of the kind displayed when using the system in a laboratory.

To complete this system, a complete procedure for use by inspectors has been devised. It comprises a rolling programme which guides the operator to carry out the fitting, the verification and the removal of a sealing-bolt, either in the laboratory (by means of a reading head on a stand) or, much more significantly, on site, namely above the storage "pond" of a nuclear installation, as in FIG. 10.

In FIG. 10, a storage "pond" is shown in which are emersed a number of storage containers 100. There is a pond handler 101 which extends across the width of the pond on which an inspection unit 102 is located. The pond handler 101 is driven by a driver 103 which is capable of sliding the pond handler 101 along the length of the pond to access the various containers 100. The container under inspection 104 is illuminated by an underwater spotlight 105 and monitored by an underwater CCTV 106. Inspectors 107 and 108 are able to operate the instrumentation on inspection unit 102.

Figure 11:
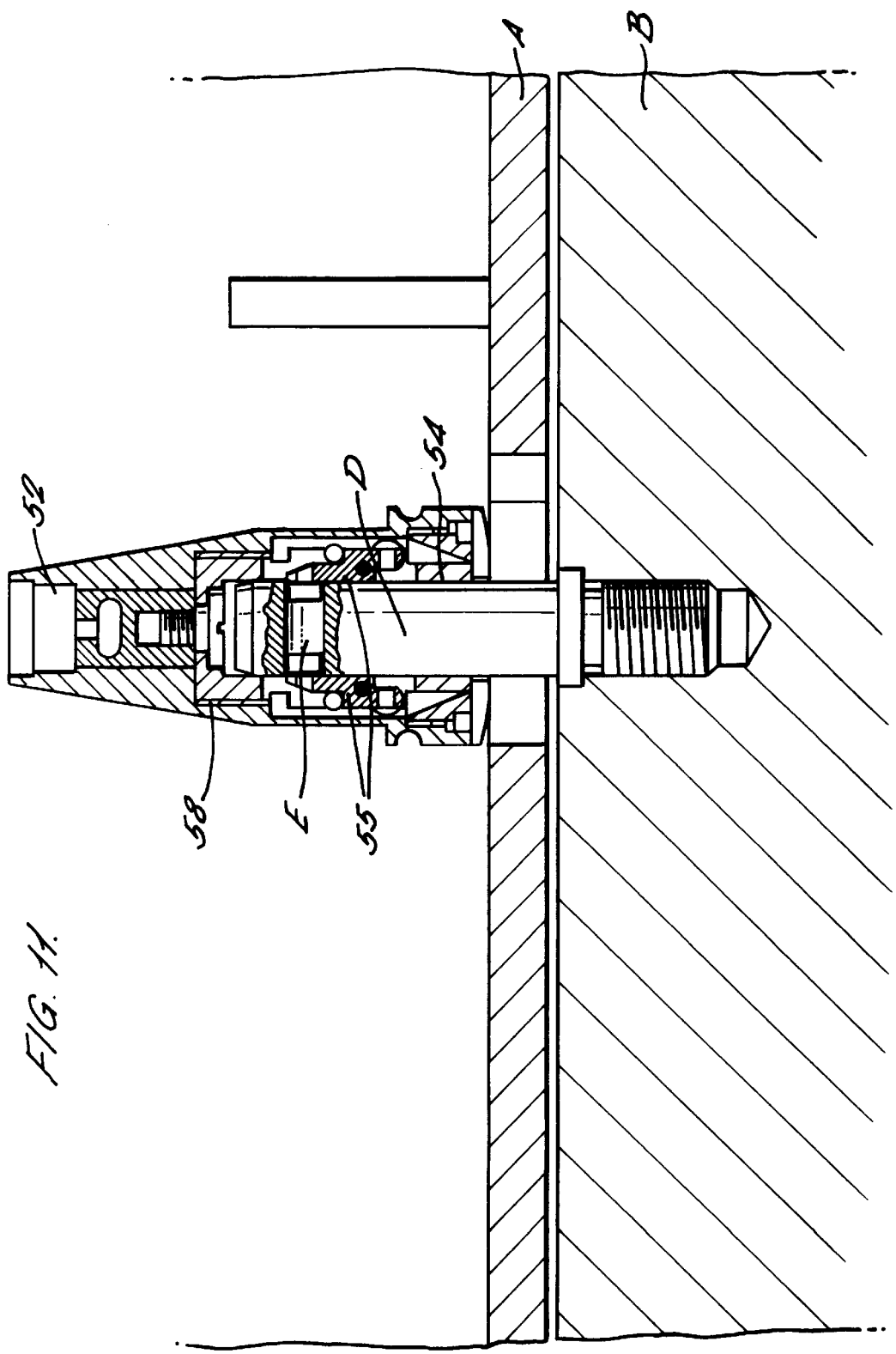
FIG. 11 depicts an alternative sealing bolt in accordance with the present invention.

FIG. 11 depicts an alternative embodiment of a sealing bolt means in accordance with the present invention. In this embodiment, the body of the sealing bolt means comprises hollow shaft 54 and pivotally mounted clamping elements 55 rather than a reverse threaded shank. There is a pre-installed dowel or pin D corresponding to shank 4 described above having a transversal hole E therethrough. Clamping elements 55 radially pivot and lock into the transversal hole E when the outer head is placed over the dowel. As in the FIG. 2a embodiment, an internal thread 58 is the axial reaction means for causing breaking of the frangible element 1a (not shown) in core 52. The clamping elements 55 ensure that the lid A (or upper collar) cannot be separated from the body B (or shock-absorber) until the frangible element is broken.

In FIG. 11, the transverse hole E and clamping elements 55 could alternatively by replaced by an internal thread which could co-operate with a threaded dowel or pin extending from the container.

Figure 12B:
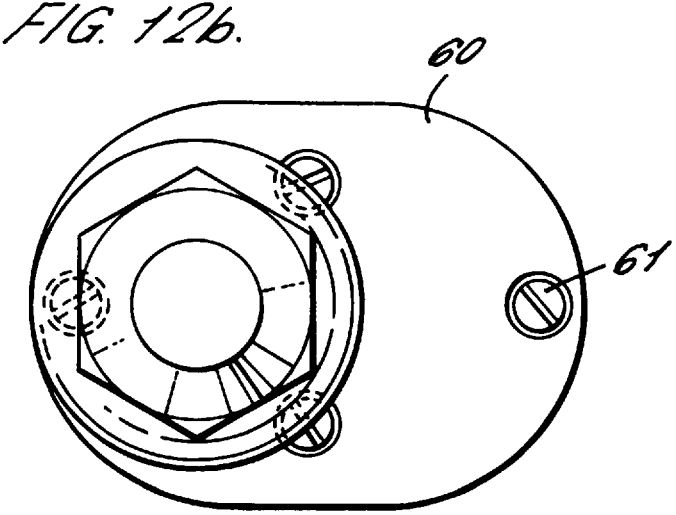

FIGS. 12a and 12b depict a sealing bolt Y in accordance with the present invention which has been secured to a structure by an intermediate plate 60. The intermediate plate 60 is used when the sealing bolt cannot be secured directly to a container or structure because the container/structure cannot be drilled to accept the shank 4 of the sealing bolt. The intermediate plate 60 is attached to the container/structure A by means of four screws 61. The head 1 of the sealing bolt should be secured to the intermediate plate 60 such that it overlaps at least one of the screws 61, thereby preventing removal of the intermediate plate without tampering with the sealing bolt. An O-ring 62 is provided between the head 1 and intermediate plate 60. This type of identification is referred to as "tagging". FIG. 12a is a side view for the sealing bolt in position on a container/structure (A) and FIG. 12b is a view from above in direction Z in FIG. 12a.

Figure 13:
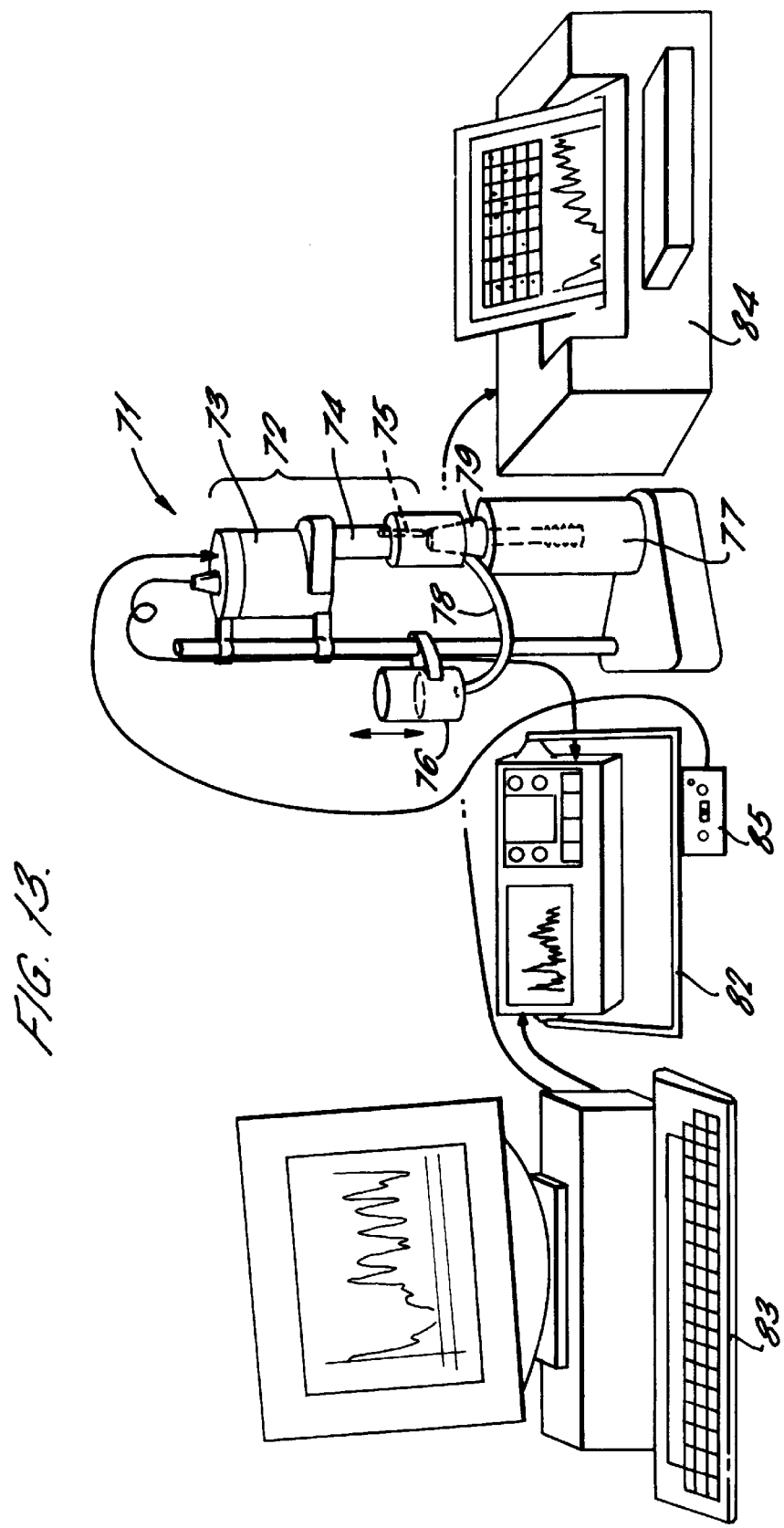
FIG. 13 depicts an ultrasonic testing system in accordance with a preferred embodiment of the present invention.

Finally, FIG. 13 depicts an ultrasonic testing system in accordance with the present invention in use on a laboratory workbench.

The testing system shown in FIG. 13 includes the sealing bolt reading device 71 comprising a reading head 72, a motor/reducer box 73, an adapter 74 and a rotating transducer 75.

A sealing bolt holder 77 is located below the motor/reducer box 73. A vertically moveable water vessel 76 is able to pour water between the rotating transducer 75 and the sealing bolt holder 77. A flexible water tubing 78 connects the water vessel 76 with the holder 77. The sealing bolt 79 under measurement is located below the rotating transducer 75. An ultrasonic flaw detector 82 is also provided—this device could be replaced by electronic boards in a laptop computer. A PC 83 is located with the necessary software to control the verification operations and a printer 84 prints the protocol of each measurement (curves and operating parameters). The control switch 85 controls the motor which drives the rotating transducer 75.

The advantages of the present invention are as follows:

The sealing-bolt is incorporated in the structure of a normal bolt and can replace it.

It requires no modification to the container or to the cover/lid.

It uses random, permanent internal signature identifiers and materials which are resistant to radiation.

This original type of marking or identifier is suitable for standardised manufacturing but which nevertheless allows the production of large series of random signatures or identities. This constitutes one element of the invention.

It is robust and shock-resistant.

Its unique identity and its integrity can be read in the course of a single reading.

If a sealing-bolt is untightened or an attempt is made to do so, its integrity is violated and this can be recognised.

The associated equipment is simple to use and is suitable for use in "ponds" and dry conditions as well. Furthermore, the essential functions of the ultrasonic equipment can be installed in electronic cards suitable for installation into portable computers.

The breaking mechanism is incorporated in the sealing-bolt.

Merely unscrewing the bolt causes its integrity to be violated.

It is able to serve as an identification means, i.e mounting on a structure to be identified without it having a "sealing" function.

It is also suitable for reading in the open air, which is a great advantage if it is intended to secure such a bolt, for example, as a "marker" to a military tank or for sealing dry storage containers.

We claim:

1. A sealing fastener comprising:
   a unique identifier within the fastener;
   a fastener loosening attempt or removal indicator within the fastener;
   said identifier comprising a unique ultrasonically detectably ultrasonic signature producing pattern of cavities in a core structure;
   said indicator comprising a frangible element providing an ultrasonically detectable signature when broken;
   said fastener being installable in an element to be sealed by a first motion and removable from such element by a second motion carried out beyond an initial portion of said second motion;
   said frangible element arranged in the fastener so as to be rupturable upon the occurrence of said initial portion of said second motion.

2. The sealing fastener according to claim 1, said fastener comprising a bolt including a head portion and threaded shank;
  said identifier and indicator being contained in a driving connection device coupled to said head so as to transmit first and second motions applied to said driving connection to said head;
  said driving connection device including a first section connectable to a fastener driving device and a second section connectable to said head, said head being drivable at least in said second direction by transmittal of second motion to said head via the first and second sections of the driving connection;
  said second section being connected to said frangible element and being connected to said first section so as to be displaced relative to the first section upon the movement over the initial portion of said second motion by said first section while said head remains stationary;
  said frangible element spanning said first and second sections and located so as to be broken upon the occurrence of said relative displacement between said first and second sections.

3. A sealing fastener as claimed in claim 2, including a one-way drive device located between said head and said second section and arranged to transmit first motion applied to said driving connection device to said head, but to disengage the connection driving device from the head when second motion is applied to the driving connection device.

4. A sealing fastener according to claim 2, said fastener having a longitudinal axis; said driving connection device including a conical outer surface symmetrically located relative to said axis.

5. A sealing fastener according to claim 2, wherein said identifier and said indicator are integrated as a singular structural element constituted of a metallic core structure.

6. A sealing fastener according to claim 5, wherein said identifier comprises a stacked assembly of metallic washer elements each having at least one ultrasonically detectable cavity, wherein the washers are assembled with the respective cavities randomly oriented relative to the cavities of other washers of the assembly to produce said unique ultrasonic signature pattern of cavities, said pattern being unique to an individual identifier.

7. A sealing fastener according to claim 6, wherein said fastener has a central longitudinal axis; and said frangible element is located eccentrically of said axis.

8. A sealing fastener according to claim 1, wherein said identifier and said indicator are integrated as a single structural element constituted of a metallic core structure.

9. A sealing fastener according to claim 8, wherein said unique identifier comprises a stacked assembly of metallic washer elements each having at least one ultrasonically detectable cavity, wherein the washer elements are assembled with their respective cavities randomly oriented relative to the cavities of the other washer elements of the assembly to produce said unique ultrasonic signature pattern of cavities, said pattern being unique to an individual identifier.

10. A sealing fastener according to claim 9, wherein said fastener has a central longitudinal axis; and said frangible element is located eccentrically of said axis.

11. A sealing fastener according to claim 10, said fastener including a driving connection device, said driving connection device including a conical shaped outer surface symmetrically located relative to said longitudinal axis with the smaller diameter of the conical surface facing away from the fastener.

12. An ultrasonic sealing fastener identification and removal or loosening indicator system, comprising:
  a sealing fastener including a unique identifier within the fastener;
  a fastener loosening attempt or removal indicator within the fastener;
  said identifier comprising a unique ultrasonically detectably ultrasonic signature producing pattern of cavities in a core structure;
  said indicator comprising a frangible element providing an ultrasonically detectable signature when broken;
  said fastener being installable in an element to be sealed by a first motion and removable from such element by a second motion carried out beyond an initial portion of said second motion;
  said frangible element arranged in the fastener so as to be rupturable upon the occurrence of said initial portion of said second motion;
  a driving connection device connected to the fastener for transmitting first and second motions from a fastener driving device to the fastener;
  an ultrasonic energy transmitting and receiving device including a coupling element arranged to engage the driving connection device and to be positioned upon such engagement in a predetermined location relative to said fastener;
  said ultrasonic device being arranged to generate fault signals corresponding to ultrasonic signatures of said identifier and said indicator at said predetermined location.

13. An ultrasonic system according to claim 12,
  said fastener including a longitudinal axis;
  said driving connection device including a conical portion symmetrically located relative to said axis with the smaller diameter of the conical portion extending away from the fastener;
  said coupling element including a conical cavity configured to receive said conical portion in close-fitting relationship;
  said ultrasonic energy transmitting and receiving device including an ultrasonic transducer located eccentrically of said longitudinal axis in close proximity to said coupling element;
  said indicator being located eccentrically of said axis; and
  a transducer motion producer for causing orbital motion of the transducer about said axis.

14. An ultrasonic system according to claim 13, said ultrasonic energy transmitter and receiving device being disposed in a reading head, and including at least one extension tube connected to said reading head for enabling remote manipulation or guidance of said reading head.

15. A method of ultrasonically identifying individual sealing fasteners and detecting attempts to loosen or remove such fasteners, comprising the steps of:
  providing a sealing fastener including a unique ultrasonic identifier for the individual fastener, said identifier producing a unique ultrasonic signature when subjected to signals produced by an ultrasonic fault measuring device;
  providing the sealing fastener with a frangible fastener loosening attempt or removal indicator, such indicator producing an ultrasonic signature when subjected to signal produced by an ultrasonic fault measuring device indicative of the integrity of the indicator;

providing the fastener with at least two sections that are relatively movable upon attempted loosening of the fastener following installation of the fastener on a device to be sealed and connecting the indicator between the relatively movable sections such that relative movement resulting from an attempted fastener loosening or removal breaks the frangible element;

installing the fastener at a desired location on a device to be sealed and securing the fastener against loosening;

subjecting the fastener identifier and indicator to signals produced by an ultrasonic fault measuring device located in close proximity to said identifier and indicator such that clear ultrasonic signatures of the identifier and indicator are obtained.

16. A method according to claim 15, including providing said sealing fastener with a conical driving connection portion located symmetrically along a longitudinal axis of the fastener and providing the ultrasonic fault measuring device with a conical cavity arranged to receive the conical driving connection portion in close fitting relationship and having an ultrasonic transducer in close proximity to said cavity but located eccentrically of the axis of the cavity;

locating the indicator in the fastener eccentrically of the fastener axis; and subjecting the indicator to said ultrasonic signals while causing orbital motion of the transducer about said fastener axis.

17. An ultrasonic fault measuring device comprising:

a reading head having an ultrasonic transducer therein;

said reading head including a conical cavity having an axis of symmetry;

said transducer located in close proximity to said cavity and eccentrically of said axis;

said transducer also located to project ultrasonic signals into the cavity along the direction of said axis; and a device for causing orbital motion of the transducer about said axis while the transducer is energized to produce fault measuring signals.

\* \* \* \* \*